US006593481B1

(12) United States Patent
Manzer

(10) Patent No.: US 6,593,481 B1
(45) Date of Patent: Jul. 15, 2003

(54) HYDROGENATION OF 3,4-TETRAHYDROFURANDIOL TO TETRAHYDROFURAN

(75) Inventor: Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/292,557

(22) Filed: Nov. 12, 2002

Related U.S. Application Data

(60) Provisional application No. 60/348,863, filed on Nov. 13, 2001.

(51) Int. Cl.[7] ............................................. C07D 307/02
(52) U.S. Cl. ..................... 549/509; 549/505; 549/507
(58) Field of Search ................................ 549/429, 505, 549/507, 509

(56) References Cited

U.S. PATENT DOCUMENTS

| 4,313,884 A | 2/1982 | Arena |
| 4,401,823 A | 8/1983 | Arena |
| 4,939,277 A | 7/1990 | Imaki et al. |
| 6,013,812 A | 1/2000 | Haas et al. |

OTHER PUBLICATIONS

Hudson, B. G. and Barker, Robert, The Conversion of Acylic Carbohydrates of Tetrahydrofuran Derivatives. The Acid-–Catalyzed Degydration of Tetritols and Pentitols, Journal of Organic Chemistry, 1967, 32,11, pp. 3650–3658.

Montassier, C, Ménézo, J. C., Moukolo, J., Naja, J., Hoang, L. C., Barbier, J. and Boitiaux, J. P., Polyol conversions into furanic dervatives on bimetallic catalysts: Cu–Ru, Cu–Pt and Ru–Cu, Journal of Molecular Catalysis, 1991, 70, pp. 65–84. Elsevier Sequoia, Lausanne.

Braca, Giuseppe, Raspolli, Anna Maria and Sbrana, Glauco, Anionic ruthenium iodocarbonyl complexes as selective dehydroxylation catalysts in aqueous solution, Journal or Organometallic Chemistry, 1991, 417, 41–49, Elsevier Sequoia S.A.

*Primary Examiner*—Amelia Owens
(74) *Attorney, Agent, or Firm*—Inna Y. Belopolsky

(57) ABSTRACT

Disclosed is a method whereby 3,4-tetrahydrofurandiol is hydrogenated in the presence of Rh, Re, Pd, Ru and Ni catalysts, optionally supported, to form tetrahydrofuran and its precursors.

32 Claims, No Drawings

HYDROGENATION OF 3,4-TETRAHYDROFURANDIOL TO TETRAHYDROFURAN

FIELD OF INVENTION 3,4-Tetrahydrofurandiol is hydrogenated in the presence of metal catalysts to form tetrahydrofuran and precursors.

BACKGROUND

Tetrahydrofuran is an industrially important solvent and monomer. Commercially it is prepared from nonrenewable petrochemical feedstocks. With the potential depletion of the world's oil reserves, a need exists to develop a source of tetrahydrofuran from renewable sources such as biomass. Biomass comprises primarily a carbohydrate containing material. Biomass can also mean as comprising a polysaccharide material. It can also mean comprising cellulose, hemicellulose, or lignocellulose materials: for example, the biomass as obtained from wood, plants, residue from agriculture or forestry, organic component of municipal and industrial wastes, primary sludges from paper manufacture, waste paper, waste wood (e.g., sawdust), agricultural residues such as corn husks, corn cobs, rice hulls, straw, bagasse, starch from corn, wheat oats, and barley, waste plant material from hard wood or beech bark, fiberboard industry waste water, bagasse pity, bagasse, molasses, post-fermentation liquor, furfural still residues, aqueous oak wood extracts, rice hull, oats residues, wood sugar slops, fir sawdust, naphta, corncob furfural residue, cotton balls, rice, straw, soybean skin, soybean oil residue, corn husks, cotton stems, cottonseed hulls, starch, potatoes, sweet potatoes, lactose, waste wood pulping residues, sunflower seed husks, hexose sugars, pentose sugars, sucrose from sugar cane and sugar beets, corn syrup, hemp, and combinations of the above. Carbohydrates offer a convenient starting material, with their multiple reactive hydroxyl groups, but a drawback of using most carbohydrates is the need to remove the unwanted hydroxyls.

1,2,3,4-Tetrahydroxybutane is a 4-carbon sugar alcohol, or tetritol, and can have three isomeric forms: erythritol, the meso form; D-threitol and L-threitol. Erythritol is used as a low calorie sweetener and sugar substitute and is typically produced commercially via the fermentation of corn starch. Threitol has limited commercial manufacture or use, but can be produced via modification of the equivalent isomer of tartaric acid. All the isomeric forms of 1,2,3,4-tetrahydroxybutane are easily cyclodehydrated to form anhydroerythritol or anhydrothreitol, which are isomeric forms of 3,4-tetrahydrofurandiol.

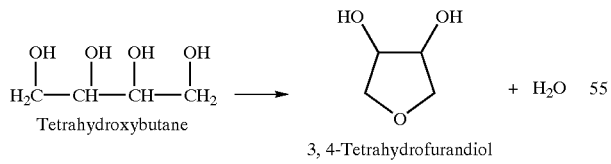

Tetrahydroxybutane → 3,4-Tetrahydrofurandiol + $H_2O$

Much work has been done on the dehydration of erythritol to various products including anhydroerythritol (U.S. Pat. No. 4,939,277, Hudson et al. (*J. Org. Chem.* (1967), 32(11), p3650), Montassier, et al., (*J. Mol. Catal.* (1991), 70(1), p65), Braca, et al, (*J. Organomet Chem.* (1991), 417(1–2), p41)), but little or no tetrahydrofuran was prepared.

U.S. Pat. No. 6,013,812 describes a process for the cyclodehydration of a 4-carbon polyol in the presence of a supported metal catalyst, an acid catalyst and added water, producing a mixture of various hydroxylated cyclic ethers. U.S. Pat. No. 4,401,823 uses carbonaceous pyropolymer impregnated with a transition metal to hydrogenate polyols to produce a large variety of compounds. U.S. Pat. No. 4,313,884 prepares anhydropolyols from the corresponding polypls using various metal ions as catalysts; however no examples are described using erythritol.

SUMMARY OF THE INVENTION

The invention is directed towards a process to prepare tetrahydrofuran and precursors to tetrahydrofuran comprising: contacting 3,4-tetrahydrofurandiol with a catalytic amount of at least one metal catalyst. In a preferred embodiment, the process comprises contacting anhydroerythritol with a catalytic amount of one or more metals selected from Periodic Group 8, where the metal is optionally supported on a solid support. Preferably the metal is selected from the group consisting Rh, Re, Pd, Ru and Ni. A preferred support is carbon and a preferred metal is Re.

The invention may additionally comprise a metal promoter, preferably selected from Periodic Groups 8, 11, and 12 metals, and Sn and Pb. More preferably, the promoter is selected from the group consisting of Zn, Cd, Sn, Pb, Cu, Ag, Au, and Pt, most preferably Pt, Au, or Ru.

In one embodiment, the invention further comprises the conversion to tetrahydrofuran of the precursors. In another embodiment, the unsaturated precursors are recycled back into the said process.

The invention is also directed towards a process to prepare tetrahydrofuran and unsaturated precursors of tetrahydrofuran comprising the steps of:

a) converting 1,2,3,4-tetrahydroxybutane to 3,4-tetrahydrofurandiol;

b) optionally separating the 3,4-tetrahydrofurandiol; and c) contacting 3,4-tetrahydrofurandiol with a catalytic amount of at least one metal catalyst.

DETAILED DESCRIPTION OF THE INVENTION

The invention is a process to prepare tetrahydrofuran and its precursors by contacting 3,4-tetrahydrofurandiol with a catalytic amount of one or more metals. Preferably the metals are from Periodic Group 8; more preferably the metals are selected from the group consisting Rh, Re, Pd, Ru and Ni. By "3,4-tetrahydrofurandiol" is meant any optical isomer, or mixture thereof of the compound shown below:

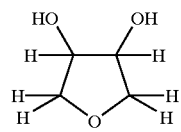

Various isomers of 3,4-tetrahydrofurandiol include anhydroerythritol and anhydrothreitol. A preferred isomer is erythritol.

By "precursors" herein is meant butanediol, unsaturated furans, and hydroxylated forms of tetrahydrofuran and unsaturated furans, as represented by Formulae I, II, and III below wherein each R is independently hydrogen and OH, and their isomeric forms. Preferred precursors are furan and 1,4-dihydrofuran.

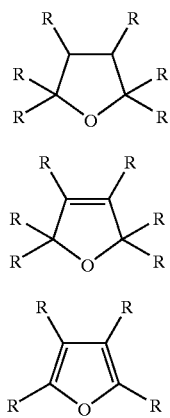

The process of the instant invention may further comprise the conversion of the precursors of tetrahydrofuran. This may be done by any of the methods known in the art. See Ullmann's Encyclopedia of Industrial Chemistry, 5$^{th}$ Ed., Vol. A26, pp. 222–223 for a description of many of these methods. The instant process may also comprise the recycling of the precursors back into the process for further conversion to tetrahydrofuran.

The process of the instant invention may additionally comprise converting 1,2,3,4-tetrahydrobutane to 3,4-tetrahydrofurandiol; optionally separating the 3,4-tetrahydrofurandiol; and then contacting the 3,4-tetrahydrofurandiol with a catalytic amount of one or more metals from Periodic Group 8 to prepare tetrahydrofuran and unsaturated precursors of tetrahydrofuran. A preferred process comprises the conversion of erythritol to anhydroerythritol. Preferred metals are selected from the group consisting of Rh, Re, Pd, Ru and Ni. The conversion of erythritol to 3,4-tetrahydrofurandiol may be done by any method known in the art. See Advances in Carbohydrate Chemistry, S. Soltzberg, Vol. 25, pg. 229–231, 1970 for a description of many of these methods. The anhydroerythritol may be isolated before contact with the metal catalyst. This can be done by any method known in the art, such as distillation, decantation, recrystallization, or extraction.

The metal catalyst can optionally contain a promoter, preferably a metal selected from the group consisting of Periodic Group 8, 11, and 12 metals, and Sn and Pb. By "promoter" herein is meant a metal that is present at levels less than 50% by weight of the major metal.

Preferred are Au, Zn, Cd, Sn, Pb, Cu, Ag, Pt, and Au. More preferred are Pt and Au. A preferred metal catalyst is Re; more preferred is Re with a metal promoter being Ru, Rh, Pd, Ni, Pt, Au.

Suitable preferred solid supports include $SiO_2$ (silica), $Al_2O_3$ (alumina), $TiO_2$ (titania), MgO (magnesia) or $ZrO_2$ (zirconia), zeolites, carbon, clays, or mixtures thereof. Preferred solid supports are those which are neutral and have low surface areas. Commonly used techniques for treatment of supports with metal catalysts can be found in B. C. Gates, *Heterogeneous Catalysis*, Vol. 2, pp. 1–29, Ed. B. L. Shapiro, Texas A & M University Press, College Station, Tex., 1984. Preferred solid supports include carbon, $Al_2O_3$, and $SiO_2$. A more preferred solid support is carbon. More preferred carbons are those with a surface area>200 m$^2$/gm. The catalyst support can be in the form of powder, granules, pellets, or the like. Selection of an optimal average particle size for the catalyst will depend upon such process parameters as reactor residence time and desired reactor flow rates.

The metal catalyst preferably should contain about 1% to about 50% by weight total metal (catalysts and promoters) on the solid support; more preferably about 5% to about 20%. The relative percentages of the promoter may vary, but should preferably be less than or equal to 50% of the metal catalyst.

The metal catalyst can be prepared by any method known in the art. One preferred method is by impregnating the catalyst support by incipient wetness with one or more metal salts, followed by calcination.

The process is preferably performed in the liquid phase, and can be performed in any suitable reactor such as but not limited to a fixed bed, slurry, fixed plug, and a trickle bed reactor system. The reaction temperature is preferably about 100° C. to about 300° C., more preferably about 150° C. to about 250° C., most preferably 200° C. The process is preferably performed at pressures of about 100 psi (0.69 MPa) to about 2000 psi (13.8 MPa), preferably at about 500 psi (3.4 MPa).

The choice of solvent or mixture of solvents is not critical provided the solvent is not detrimental to catalyst, reactant and product. The solvent can also consist partially or totally of the recycled precursors.

It will be appreciated that the selectivities and yields of product may be enhanced by additional contact with the metal catalyst. For example, yields and selectivities may be increased where the reactor effluent containing a mixture of reactant and product may be passed one or more times over the metal catalyst under the reaction conditions to enhance the conversion of reactant to product.

The process of the instant invention may additionally comprise the recovery or isolation of tetrahydrofuran and optionally one or more of the precursors. This can be done by any method known in the art, such as distillation, decantation, recrystallization, or extraction.

EXAMPLES

Materials and Methods

The following abbreviations are used herein:

| | |
|---|---|
| BDO | 1,4-Butanediol |
| DHF | 1,4-Dihydrofuran |
| EGDME | Ethylene glycol dimethylether |
| FUR | Furan |
| GBL | Gamma-butyrolactone |
| 3-HTHF | 3-hydroxytetrahydrofuran |
| tetrahydrofuran | tetrahydrofuran |
| Support | Source |
| Sibunit carbon | Boreskov Inst. of Catalysis, Novosibirsk, Russia |
| Calsicat carbon | Englehard Corp., E. Windsor, CT |
| Calgon PCB carbon | Calgon Corp. Pittsburgh, PA |

The metal catalysts were prepared using, the following general procedure. In a 150 ml beaker, a solution or slurry was made up of the metal precursors and deionized $H_2O$. The carbon support was first dried and reduced under an atmosphere of $H_2$ for 2 hours at 400° C. or 450° C. Unless otherwise specified in the Table, the carbon used was Calgon PCB. The precursors used were $NiCl_2.6H_2O$, $AuCl_3.3H_2O$ $Re_2O_7$, $PdCl_2$, $Re_2O_7$ (Alfa Aesar, Ward Hill, Mass.), $RuCl_3.xH_2O$ (Aldrich, Milwaukee, Wis.), $H_2PtCl_6$ (Johnson Matthey, Ward Hill, Mass.), and (Alfa). The support was added to the slurry. The slurry was allowed to stand at for 1 hour at room temperature with occasional stirring and then dried at 120° C. overnight with frequent stirring (until free flowing).

The reaction was performed by placing the appx. 100 mg feedstock, a solution of anhydroerythritol dissolved in the solvent listed, if used, with appx. 100 mg of the metal catalyst in a 2 ml pressure vessel. The vessel was charged with $H_2$ to the pressure shown in the Table, $N_2$ was added if necessary to bring the total pressure to 500 psi (3.4 MPa), and then the vessel was heated to 150° C., 175° C. or 200° C. for 2 hours. The vessel was then cooled, methoxyethylether was added as an internal standard and the products analyzed on an HP 6890 GC/Mass using a column of CP-Wax 58 (FFAP) 25 m×0.25 mm ID from Chrompack. By relating the areas of individual components relative to the internal standard and applying response factors the yield to each of the individual products were calculated. The selectivity (Sel) of each individual product was then calculated as the weight percent of the product in the total product weight inclusive of unreacted reactants.

TABLE 1

EXAMPLES

| Ex. | Temp (° C.) | $H_2$ Press (psi) | Catalyst | Solvent | Con (%) | FUR Sel (%) | DHF Sel (%) | tetra-hydrofuran Sel (%) | TOT Sel (%) | 3-tetra-hydrofuran Sel (%) | GBL Sel (%) | 1,4-BDO Sel (%) |
|---|---|---|---|---|---|---|---|---|---|---|---|---|
| 1 | 200 | 500 | 10% Re/1% Ni/C | Dioxane | 94.9 | 0.0 | 0.2 | 53.5 | 56.4 | 0.0 | 2.7 | 0.0 |
| 2 | 200 | 500 | 10% Re/1% Pd/C | Dioxane | 95.4 | 0.0 | 0.2 | 49.7 | 54.7 | 1.6 | 3.2 | 0.0 |
| 3 | 200 | 500 | 10% Re/1% Ru/C | Dioxane | 93.1 | 0.0 | 0.1 | 45.4 | 49.5 | 0.0 | 3.9 | 0.0 |
| 4 | 200 | 500 | 10% Re/1% Rh/C | Dioxane | 94.2 | 0.0 | 0.2 | 41.3 | 45.2 | 2.0 | 1.8 | 0.0 |
| 5 | 200 | 500 | 20% Re/Calsicat C | Dioxane | 100.0 | 0.6 | 0.0 | 39.0 | 64.8 | 1.0 | 12.3 | 11.9 |
| 6 | 200 | 500 | 10% Re/Calsicat C | Dioxane | 86.1 | 0.8 | 0.0 | 38.9 | 67.2 | 0.9 | 10.7 | 16.0 |
| 7 | 200 | 500 | 10% Re/1% Pt/C | Dioxane | 94.2 | 0.0 | 0.3 | 34.8 | 36.2 | 0.0 | 1.1 | 0.0 |
| 8 | 200 | 500 | 10% Re/Calsicat C | Dioxane | 87.8 | 0.7 | 0.0 | 34.6 | 61.6 | 0.9 | 10.4 | 15.0 |
| 9 | 200 | 500 | 10% Re/1% Au/C | Dioxane | 97.9 | 0.3 | 0.0 | 29.6 | 39.6 | 0.9 | 8.7 | 0.0 |
| 10 | 200 | 500 | 20% Re/Calsicat C | Dioxane | 95.5 | 0.7 | 0.0 | 28.5 | 47.1 | 0.9 | 9.2 | 7.8 |
| 11 | 200 | 500 | 5% Re/Calsicat C | Dioxane | 70.0 | 0.5 | 0.1 | 28.0 | 73.9 | 1.0 | 12.4 | 31.7 |
| 12 | 200 | 500 | 5% Re/Calsicat C | Dioxane | 66.8 | 0.5 | 0.1 | 25.5 | 64.8 | 0.9 | 10.1 | 27.6 |
| 13 | 200 | 500 | 20% Re/Sibunit C | Dioxane | 34.0 | 1.0 | 0.0 | 20.8 | 77.8 | 2.5 | 8.7 | 44.9 |
| 14 | 200 | 500 | 5% Rh/Calsicat C | Dioxane | 22.3 | 0.0 | 0.0 | 19.8 | 33.7 | 13.7 | 0.0 | 0.2 |
| 15 | 200 | 500 | 20% Re/Sibunit C | Dioxane | 26.5 | 1.2 | 0.0 | 18.1 | 97.2 | 3.9 | 8.7 | 65.3 |
| 16 | 200 | 500 | 5% Re/SiO$_2$ | None | 4.8 | 6.3 | 3.1 | 17.6 | 84.4 | 1.5 | 3.1 | 52.8 |
| 17 | 200 | 500 | 5% Re/Calsicat C | Dioxane | 32.9 | 2.1 | 15.9 | 16.5 | 67.7 | 1.2 | 7.7 | 24.3 |
| 18 | 200 | 500 | 5% Re/Sibunit C | None | 40.5 | 0.6 | 3.6 | 12.8 | 61.9 | 0.6 | 5.3 | 39.1 |
| 19 | 200 | 500 | 5% Re/Sibunit C | Dioxane | 16.1 | 1.0 | 1.2 | 12.5 | 91.7 | 1.1 | 9.0 | 66.9 |
| 20 | 200 | 500 | 5% Re/Calsicat C | None | 86.6 | 0.4 | 2.5 | 11.6 | 16.3 | 0.3 | 1.1 | 0.5 |
| 21 | 200 | 500 | 10% Re/Sibunit C | Dioxane | 40.9 | 0.5 | 0.3 | 10.4 | 82.1 | 1.2 | 8.7 | 60.9 |
| 22 | 200 | 500 | 10% Re/Sibunit C | Dioxane | 35.2 | 0.5 | 0.2 | 10.4 | 96.6 | 1.4 | 8.8 | 75.2 |
| 23 | 200 | 500 | 5% Re/Sibunit C | Dioxane | 25.2 | 0.4 | 0.8 | 9.3 | 88.6 | 1.0 | 7.6 | 69.6 |
| 24 | 200 | 500 | 5% Re/Calsicat C | EGDME | 99.8 | 1.4 | 15.9 | 8.4 | 29.8 | 0.3 | 3.0 | 0.8 |
| 25 | 200 | 500 | 5% Re/Al$_2$O$_3$ | EGDME | 46.0 | 1.1 | 1.8 | 8.3 | 34.3 | 1.0 | 1.9 | 20.3 |
| 26 | 200 | 500 | 5% Re/Calgon C | EGDME | 74.6 | 0.7 | 3.9 | 7.2 | 62.9 | 0.2 | 10.1 | 40.7 |
| 27 | 200 | 500 | 5% Re/Sibunit C | EGDME | 70.4 | 0.8 | 5.4 | 7.0 | 54.4 | 0.3 | 7.0 | 33.9 |
| 28 | 175 | 500 | 5% Re/Sibunit C | EGDME | 42.3 | 0.3 | 8.4 | 6.7 | 28.7 | 0.1 | 1.2 | 11.9 |
| 29 | 200 | 500 | 5% Re/Calgon C | None | 62.1 | 0.3 | 0.7 | 6.2 | 55.9 | 0.3 | 2.3 | 46.1 |
| 30 | 150 | 500 | 5% Re/Calgon C | EGDME | 45.6 | 0.2 | 15.5 | 6.1 | 37.0 | 0.0 | 1.6 | 13.6 |
| 31 | 175 | 500 | 5% Re/Calsicat C | EGDME | 100.0 | 0.6 | 26.8 | 6.1 | 35.8 | 0.1 | 1.3 | 0.9 |
| 32 | 150 | 500 | 5% Re/Sibunit C | EGDME | 27.9 | 0.5 | 3.2 | 6.0 | 17.2 | 0.0 | 0.5 | 7.1 |
| 33 | 200 | 500 | 5% Rh/Sibunit C | Dioxane | 8.7 | 0.7 | 5.1 | 5.9 | 44.9 | 33.2 | 0.0 | 0.0 |
| 34 | 150 | 500 | 5% Re/Al$_2$O$_3$ | EGDME | 29.8 | 0.3 | 1.1 | 5.6 | 15.4 | 0.1 | 0.3 | 7.9 |
| 35 | 200 | 500 | 5% Re/Al$_2$O$_3$ | Dioxane | 10.8 | 2.0 | 5.6 | 5.3 | 78.2 | 2.1 | 4.7 | 58.5 |
| 36 | 200 | 500 | 5% Re/Al$_2$O$_3$ | None | 29.5 | 0.3 | 0.7 | 4.9 | 40.0 | 0.8 | 1.6 | 31.7 |
| 37 | 200 | 500 | 5% Rh/Calgon C | Dioxane | 4.4 | 0.8 | 0.0 | 4.5 | 37.3 | 32.1 | 0.0 | 0.0 |
| 38 | 175 | 500 | 5% Re/Calgon C | EGDME | 61.3 | 0.3 | 11.8 | 4.5 | 42.9 | 0.1 | 3.9 | 22.4 |
| 39 | 200 | 500 | 5% Re/SiO$_2$ | Dioxane | 2.2 | 0.0 | 16.0 | 4.5 | 40.1 | 0.0 | 2.3 | 17.4 |
| 40 | 200 | 60 | 5% Re/SiO$_2$ | None | 12.5 | 0.8 | 10.3 | 4.3 | 22.8 | 0.0 | 1.1 | 6.1 |
| 41 | 175 | 500 | 5% Re/Al$_2$O$_3$ | EGDME | 43.4 | 0.3 | 1.5 | 4.0 | 16.2 | 0.3 | 0.4 | 9.7 |
| 42 | 200 | 500 | 5% Re/Calgon C | Dioxane | 22.7 | 0.3 | 6.7 | 4.0 | 66.7 | 0.5 | 7.7 | 47.5 |
| 43 | 150 | 500 | 5% Re/Calsicat C | EGDME | 67.1 | 0.3 | 39.8 | 4.0 | 45.4 | 0.1 | 0.3 | 0.9 |
| 44 | 200 | 500 | 5% Re/Sibunit C | Dioxane | 11.8 | 2.4 | 16.7 | 3.7 | 81.8 | 0.9 | 8.0 | 50.1 |
| 45 | 200 | 500 | 5% Re/SiO$_2$ | EGDME | 23.6 | 0.9 | 1.9 | 3.6 | 12.8 | 0.3 | 0.6 | 5.6 |
| 46 | 200 | 500 | 5% Ni/Calsicat C | Dioxane | 2.4 | 1.2 | 1.6 | 2.8 | 5.6 | 0.0 | 0.0 | 0.0 |
| 47 | 200 | 500 | 5% Rh/Calsicat C | EGDME | 35.0 | 0.3 | 0.0 | 2.7 | 12.0 | 8.5 | 0.3 | 0.2 |
| 48 | 200 | 500 | 5% Pd/Sibunit C | None | 35.7 | 0.0 | 0.0 | 2.6 | 19.8 | 17.2 | 0.0 | 0.0 |
| 49 | 200 | 60 | 5% Re/Al$_2$O$_3$ | None | 35.3 | 0.8 | 6.2 | 2.5 | 23.3 | 0.3 | 3.6 | 9.8 |
| 50 | 200 | 500 | 5% Ni/SiO$_2$ | Dioxane | 2.6 | 0.0 | 8.0 | 2.2 | 12.0 | 1.8 | 0.0 | 0.0 |
| 51 | 200 | 500 | 5% Pd/Calgon C | None | 39.8 | 0.1 | 0.0 | 2.1 | 14.3 | 12.2 | 0.0 | 0.0 |
| 52 | 200 | 500 | 5% Ni/Sibunit C | Dioxane | 6.9 | 0.8 | 1.6 | 1.9 | 4.2 | 0.0 | 0.0 | 0.0 |
| 53 | 175 | 500 | 5% Re/SiO$_2$ | EGDME | 32.7 | 0.4 | 3.5 | 1.8 | 7.5 | 0.0 | 0.2 | 1.6 |
| 54 | 200 | 500 | 5% Rh/Al$_2$O$_3$ | Dioxane | 59.3 | 0.1 | 0.0 | 1.8 | 12.9 | 11.0 | 0.0 | 0.1 |
| 55 | 200 | 500 | 5% Pd/Calsicat C | None | 64.4 | 0.4 | 0.3 | 1.6 | 7.2 | 4.9 | 0.0 | 0.0 |
| 56 | 200 | 500 | 5% Rh/Al$_2$O$_3$ | EGDME | 62.4 | 0.1 | 0.0 | 1.3 | 11.7 | 10.2 | 0.1 | 0.0 |
| 57 | 200 | 500 | 5% Rh/Sibunit C | EGDME | 19.1 | 0.5 | 0.0 | 1.1 | 11.3 | 9.3 | 0.4 | 0.0 |
| 58 | 150 | 500 | 5% Re/SiO$_2$ | EGDME | 24.2 | 0.3 | 2.7 | 1.1 | 4.8 | 0.0 | 0.3 | 0.5 |
| 59 | 200 | 500 | 5% Ni/Calgon C | Dioxane | 6.7 | 0.0 | 0.9 | 1.0 | 1.9 | 0.0 | 0.0 | 0.0 |

TABLE 1-continued

EXAMPLES

| Ex. | Temp (° C.) | H₂ Press (psi) | Catalyst | Solvent | Con (%) | FUR Sel (%) | DHF Sel (%) | tetra-hydrofuran Sel (%) | TOT Sel (%) | 3-tetra-hydrofuran Sel (%) | GBL Sel (%) | 1,4-BDO Sel (%) |
|---|---|---|---|---|---|---|---|---|---|---|---|---|
| 60 | 200 | 500 | 5% Pd/Al₂O₃ | None | 49.6 | 0.1 | 0.1 | 0.9 | 6.4 | 5.4 | 0.0 | 0.0 |
| 61 | 200 | 500 | 5% Pd/SiO₂ | None | 40.3 | 0.8 | 0.0 | 0.8 | 9.8 | 8.2 | 0.0 | 0.0 |
| 62 | 200 | 500 | 5% Rh/Calgon C | EGDME | 17.9 | 0.0 | 0.0 | 0.6 | 6.4 | 5.5 | 0.3 | 0.0 |
| 63 | 200 | 500 | 5% Rh/SiO₂ | Dioxane | 23.2 | 0.0 | 0.0 | 0.5 | 6.3 | 5.8 | 0.0 | 0.0 |
| 64 | 200 | 500 | 5% Ru/Al₂O₃ | Dioxane | 20.5 | 0.2 | 0.0 | 0.4 | 21.5 | 19.1 | 1.7 | 0.0 |
| 65 | 200 | 500 | 5% Rh/SiO₂ | EGDME | 33.0 | 0.2 | 0.0 | 0.3 | 3.9 | 3.1 | 0.4 | 0.0 |
| 66 | 200 | 500 | 5% Ru/Calsicat C | Dioxane | 51.6 | 0.1 | 0.0 | 0.2 | 8.0 | 3.1 | 4.6 | 0.0 |
| 67 | 200 | 60 | 5% Re/Calsicat C | None | 100.0 | 7.8 | 16.5 | 0.2 | 25.0 | 0.2 | 0.4 | 0.0 |
| 68 | 200 | 60 | 5% Re/Calgon C | None | 73.5 | 20.1 | 34.4 | 0.1 | 56.7 | 0.0 | 1.8 | 0.4 |
| 69 | 200 | 60 | 5% Re/Sibunit C | None | 90.6 | 7.8 | 18.1 | 0.0 | 26.0 | 0.0 | 0.1 | 0.0 |

What is claimed is:

1. A process for preparing tetrahydrofuran or a mixture of tetrahydrofuran and precursors of tetrahydrofuran, the process comprising contacting 3,4-tetrahydrofurandiol with a catalytic amount of at least one metal catalyst.

2. The process according to claim 1 wherein the 3,4-tetrahydrofurandiol is anhydroerythritol.

3. The process according to claim 1 wherein the metal catalyst is selected from the group consisting of Periodic Group 8 metals.

4. The process according to claim 1 wherein the metal catalyst is selected from the group consisting of Rh, Re, Pd, Ru and Ni.

5. The process according to claim 1 wherein the metal catalyst is supported on a solid support.

6. The process according to claim 1 further comprising converting the precursors of tetrahydrofuran to tetrahydrofuran.

7. The process according to claim 1 further comprising converting the precursors of tetrahydrofuran to tetrahydrofuran by contacting said precursors with a catalytic amount of at least one metal catalyst.

8. The process according to claim 1 wherein the metal catalyst comprises a metal promoter.

9. The process according to claim 8 wherein the metal promoter is selected from Periodic Groups 8, 11, and 12 metals, and Sn and Pb.

10. The process according to claim 8 wherein the metal promoter is selected from the group consisting of Zn, Cd, Sn, Pb, Ru, Ag, Au, and Pt.

11. The process according to claim 5 wherein the solid support is carbon.

12. The process according to claim 11 wherein the metal catalyst is Re.

13. The process according to claim 10 wherein the metal promoter is Pt, Au, or Ru.

14. The process according to claim 1 wherein the process is performed at a temperature of 100° C. to 300° C. and a pressure of 0.69 MPa to 13.8 MPa.

15. The process according to claim 1 wherein the process is performed at a temperature of 150° C. to 250° C. and a pressure of 3.0 MPa to 4.0 MPa.

16. The process according to claim 1 wherein the process is conducted in a solution selected from the group consisting of ethylene glycol dimethylether, dioxane, and mixtures thereof.

17. A process for preparing tetrahydrofuran and precursors of tetrahydrofuran, the process comprising the steps of:

a) converting 1,2,3,4-tetrahydroxybutane to 3,4-tetrahydrofurandiol;

b) optionally separating the 3,4-tetrahydrofurandiol; and d) contacting 3,4-tetrahydrofurandiol with a catalytic amount of at least one metal catalyst.

18. The process according to claim 17 wherein the 1,2,3,4-tetrahydroxybutane is erythritol and the 3,4-tetrahydrofurandiol is anhydroerythritol.

19. The process according to claim 17 wherein the metal catalyst is selected from the group consisting of Periodic Group 8 metals.

20. The process according to claim 18 wherein the metal catalyst is selected from the group consisting of Rh, Re, Pd, Ru and Ni.

21. The process according to claim 18 wherein the metal catalyst is supported on a solid support.

22. The process according to claim 18 further comprising converting the precursors of tetrahydrofuran to tetrahydrofuran.

23. The process according to claim 18 wherein the precursors of tetrahydrofuran are recycled back into said process.

24. The process according to claim 18 wherein the metal catalyst comprises a metal promoter.

25. The process according to claim 24 wherein the metal promoter is selected from Periodic Groups 8, 11, and 12 metals, and Sn and Pb.

26. The process according to claim 24 wherein the metal promoter is selected from the group consisting of Zn, Cd, Sn, Pb, Ru, Ag, Au, and Pt.

27. The process according to claim 21 wherein the solid support is carbon.

28. The process according to claim 27 wherein the metal catalyst is Re.

29. The process according to claim 26 wherein the metal promoter is Pt, Au, or Ru.

30. The process according to claim 18 wherein the process is performed at a temperature of 100° C. to 300° C. and a pressure of 0.69 MPa to 13.8 MPa.

31. The process according to claim 18 wherein the process is performed at a temperature of 150° C. to 250° C. and a pressure of 3.0 MPa to 4.0 MPa.

32. The process according to claim 18 wherein the process is performed in a solvent selected from the group consisting of ethylene glycol dimethylether, dioxane, and mixtures thereof.

* * * * *